(12) United States Patent
Chao et al.

(10) Patent No.: US 8,598,136 B2
(45) Date of Patent: Dec. 3, 2013

(54) BACULOVIRUS-MEDIATED TRANSGENE EXPRESSION IN BOTH MAMMALIAN AND INSECT CELLS

(75) Inventors: Yu-Chan Chao, Taipei (TW); Yueh-Lung Wu, Kaohsiung (TW); Carol Pei Yin Wu, Lo-Tung Township (TW); Chia-Hung Wang, Taichung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/281,810

(22) Filed: Oct. 26, 2011

(65) Prior Publication Data

US 2013/0109077 A1    May 2, 2013

(51) Int. Cl.
*C12N 15/11* (2006.01)
*C12N 15/00* (2006.01)

(52) U.S. Cl.
USPC ............................ 514/44 A; 435/320.1

(58) Field of Classification Search
None
See application file for complete search history.

(56) References Cited

U.S. PATENT DOCUMENTS 6,806,064 B2 * 10/2004 Chao ........................ 435/69.1

OTHER PUBLICATIONS

Lucifora et al, Control of Hepatitis B Virus Replication by Innate Response of HepaRG Cells, Hepatology, published online Aug. 2009, vol. 51, issue 1: 63-72.*
Lui et al, Titers of lentiviral vectors encoding shRNAs and miRNAs are reduced by different mechanisms that require distinct repair strategies, RNA, published online May 2010, 16: 1328-1339.*

* cited by examiner

*Primary Examiner* — Tracy Vivlemore
*Assistant Examiner* — Kate Poliakova
(74) *Attorney, Agent, or Firm* — Cesari and McKenna, LLP

(57) ABSTRACT

This invention relates to a method for expressing a gene in a cell. The method includes introducing into a cell an agent that inhibits one or both of miRNA pathway and antiviral defense pathway; and a baculovirus that contains a nucleic acid molecule including a gene operably linked to a promoter; and expressing the gene in the cell.

14 Claims, 10 Drawing Sheets

A)

B)

(A)

(B)

BACULOVIRUS-MEDIATED TRANSGENE EXPRESSION IN BOTH MAMMALIAN AND INSECT CELLS

BACKGROUND

Baculovirus is an insect specific virus; however, it can serve as an efficient vector for gene expressions in both insect and mammalian cells. Among all the baculoviruses, *Autographa californica* multicapsid nuclear polyhedrosis virus (AcMNPV) is the best studied. AcMNPV and *Spodoptera frugiperda* cells together constitute a widely used system for the production of many heterologous proteins, owing to the ease of producing large scale cultures of *S. frugiperda* cells. *Bombyx mori* NPV (BmNPV) is another widely used baculovirus gene expression system and can be used to express heterologous proteins in *B. mori* (silkworm) larvae with ease. Both baculoviruses have been shown capable of entering a variety of vertebrate cells, adding versatility to the baculovirus expression system. AcMNPV infects various insect species and replicates in some lepidopteran cell lines. However, this virus does not replicate or form polyhedra in *B. mori* cells and vertebrate cells.

MicroRNAs (miRNAs) are small RNA molecules (22 nucleotides) found in eukaryotic cells that regulate gene expression by interference during translation and/or post-transcription. Drosha is part of a multi-protein complex, the microprocessor, which mediates the nuclear processing of primary miRNAs into stem-loop precursors of approximately 60 to 70 nucleotides (pre-miRNAs). See, e.g., Lee et al., Nature, 525: 415-419 (2003). Pre-miRNAs are subsequently exported into cytomplasm via Exportin 5. In the cytoplasm, the pre-miRNAs are cleaved by Dicer into mature 22 nucleotide miRNAs. The mature miRNA is incorporate as a single stranded RNA into a ribonucleoprotein complex, known as the RNA-induced silencing complex. This complex directs the miRNA to the target mRNA, which leads either to translational repression or degradation of the target mRNA. See, e.g., Bartel, Cell, 116: 281-297 (2004); and Bartel and Chen, Nature Reviews Genetics, 5: 396-400 (2004).

Antiviral innate immunity system is the first line of host cell defense that can recognize and block viral infection. The innate immune system recognizes microorganisms and viruses via a number of pattern-recognition receptors (PRRs) including Toll-like receptors, RIG-I like receptors, NOD-like receptors, and cytosolic DNA sensing receptors, which can recognize different virus compounds known as pathogen-associated molecular patterns (PAMPs). After recognition, these PRRs can activate different signaling pathways and induce immune responses and produce interferon and cytokines to block viral gene expression or virus replication. See, e.g., Akiral et al., Cell, 124:783-801 (2006).

SUMMARY

This invention is based on the unexpected discovery that knocking-down certain genes in insect and mammalian cells can enhance the expression of baculovirus-transduced genes in these cells, as well as transduction efficiency.

Accordingly, described herein is a method for expressing a gene in a cell. The method includes introducing into a cell (i) an agent that inhibits one or both of miRNA pathway and antiviral defense pathway; and (ii) a baculovirus that contains a nucleic acid molecule including a gene operably linked to a promoter; and expressing the gene in the cell.

Also included in the present invention is a method for producing baculoviruses. The method includes introducing into a host cell a baculovirus and an agent that inhibits miRNA pathway; and replicating the baculovirus in the host cell, thereby producing progenies of the bacvulovirus.

The agent can be a compound that inhibits the expression of a gene or protein related to the miRNA pathway or the antiviral defense pathway. For example, the agent can be an siRNA that targets a gene in either pathway.

The details of one or more embodiments of the invention are set forth in the accompanying drawing and the description below. Other features, objects, and advantages of the invention will be apparent from the description and drawing, and from the claims.

DETAILED DESCRIPTION

Figure 1:
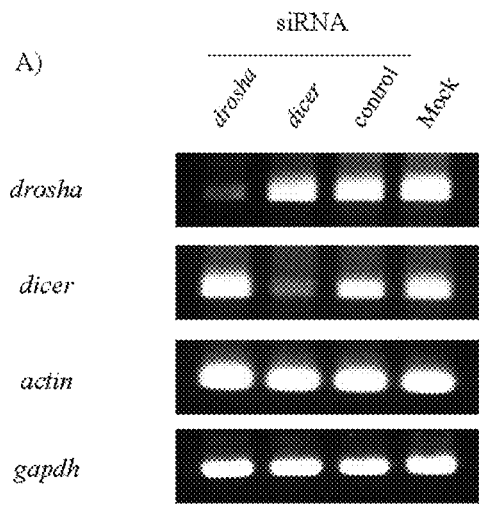
FIG. 1 is a set of photographs showing RNAi efficiency by RT-PCR in cells transfected with the indicated siRNAs. Total RNA was extracted from cells transfected with the indicated siRNAs and 1 µg of total RNA was used as template for cDNA synthesis. The expression levels of drosha and dicer in U-2OS cells (Panel A), VeroE6 cells (Panel B), and BmN cells (Panel C) were analyzed by standard PCR using synthesized cDNAs as templates. The expression levels of actin and gapdh were used as internal controls.
Figure 1:
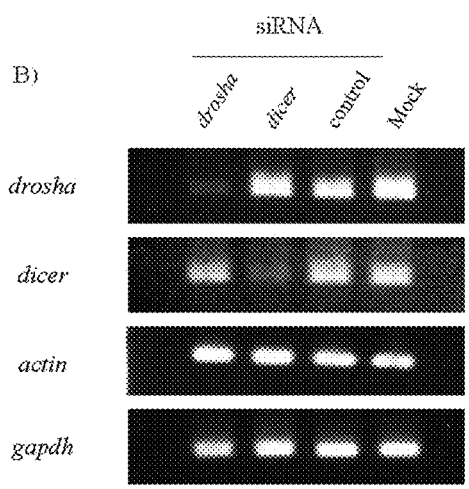
Figure 1:
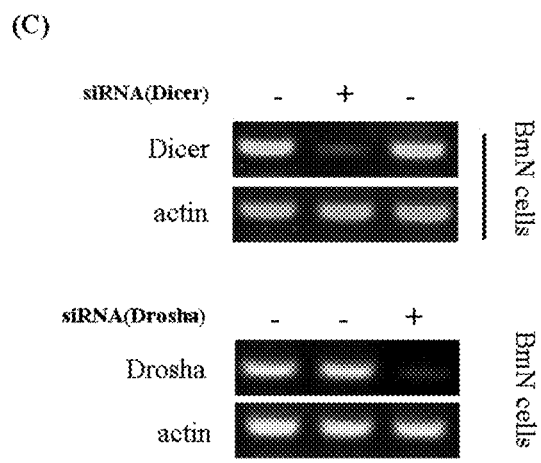
Figure 2:
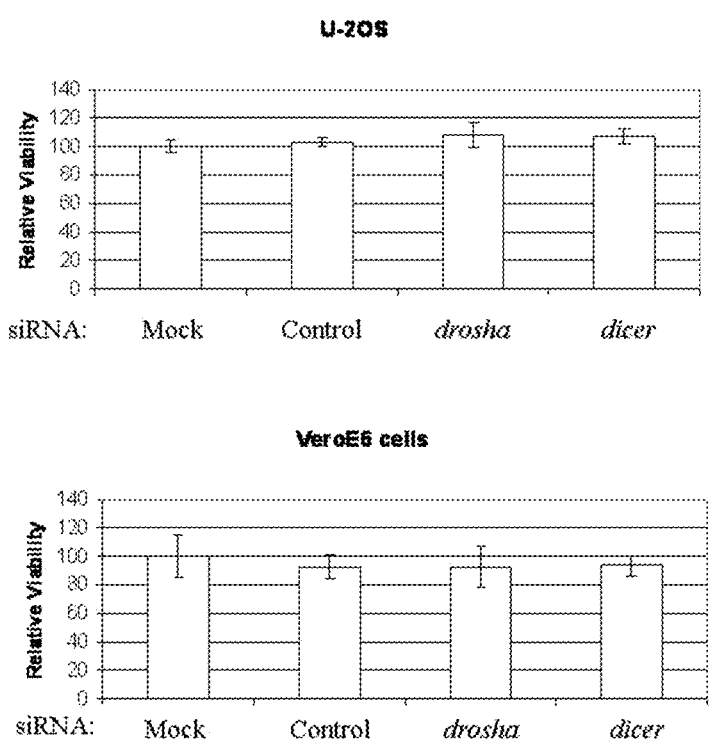
FIG. 2 is a set of bar graphs showing cell viability of U-2OS cells and VeroE6 cells transfected with siRNAs.
Figure 3:
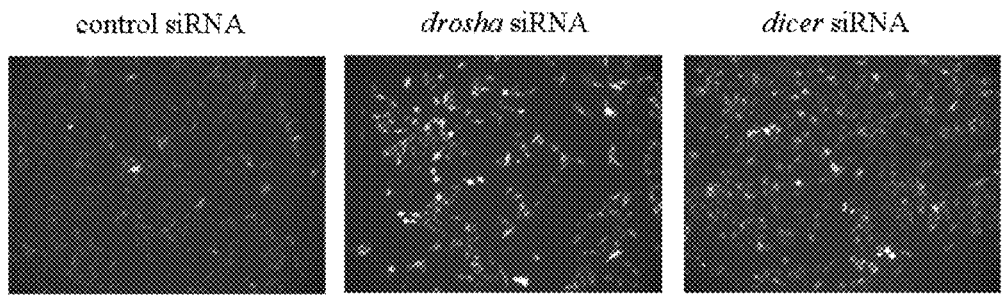
FIG. 3 is a set of fluorescent images and blots showing that knockdown of endogenous drosha or dicer expression increased GFP expression in cells transduced with a baculovirus carrying the GFP gene. Cells were transfected with the indicated siRNAs before transduction with the baculovirus. Panel A: Fluorescent images of U-2OS cells transduced by the baculovirus. Panel B: Western blots showing GFP expression in baculovirus-transduced U-2OS and VeroE6 cells.
Figure 3:
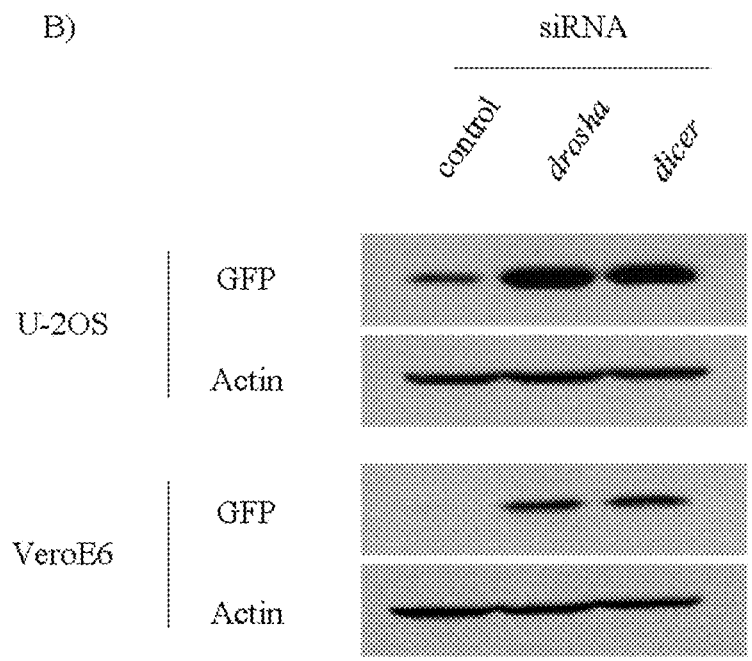
Figure 4:
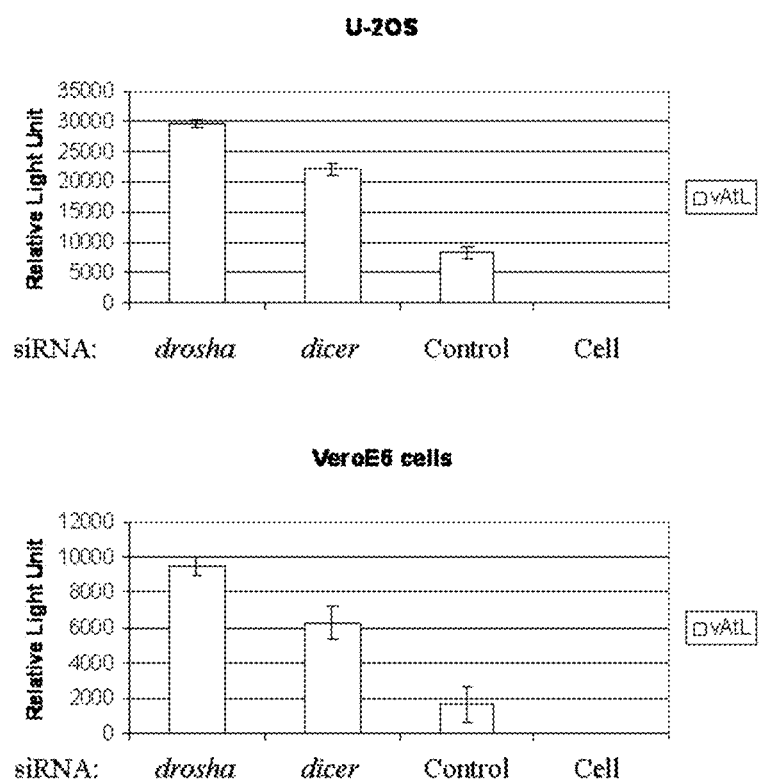
FIG. 4 is a set of bar graphs showing luciferase activity of U-2OS cells and VeroE6 cells first transfected with the indicated siRNAs and subsequently transduced with a recombinant baculovirus carrying the luciferase gene.
Figure 5:
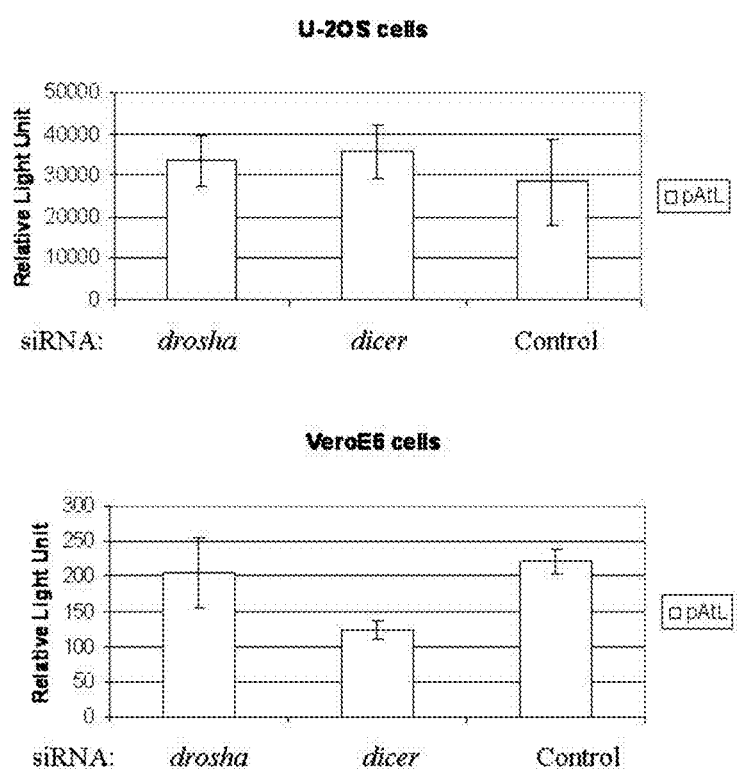
FIG. 5 is a set of graphs showing luciferase activity of U-2OS cells and VeroE6 cells first transfected with the indicated siRNAs and subsequently transfected with a plasmid carrying a luciferase-coding sequence under the control of the CMVie promoter with lipofectamine 2000 (Invitrogen) as the transfection reagent.
Figure 6:
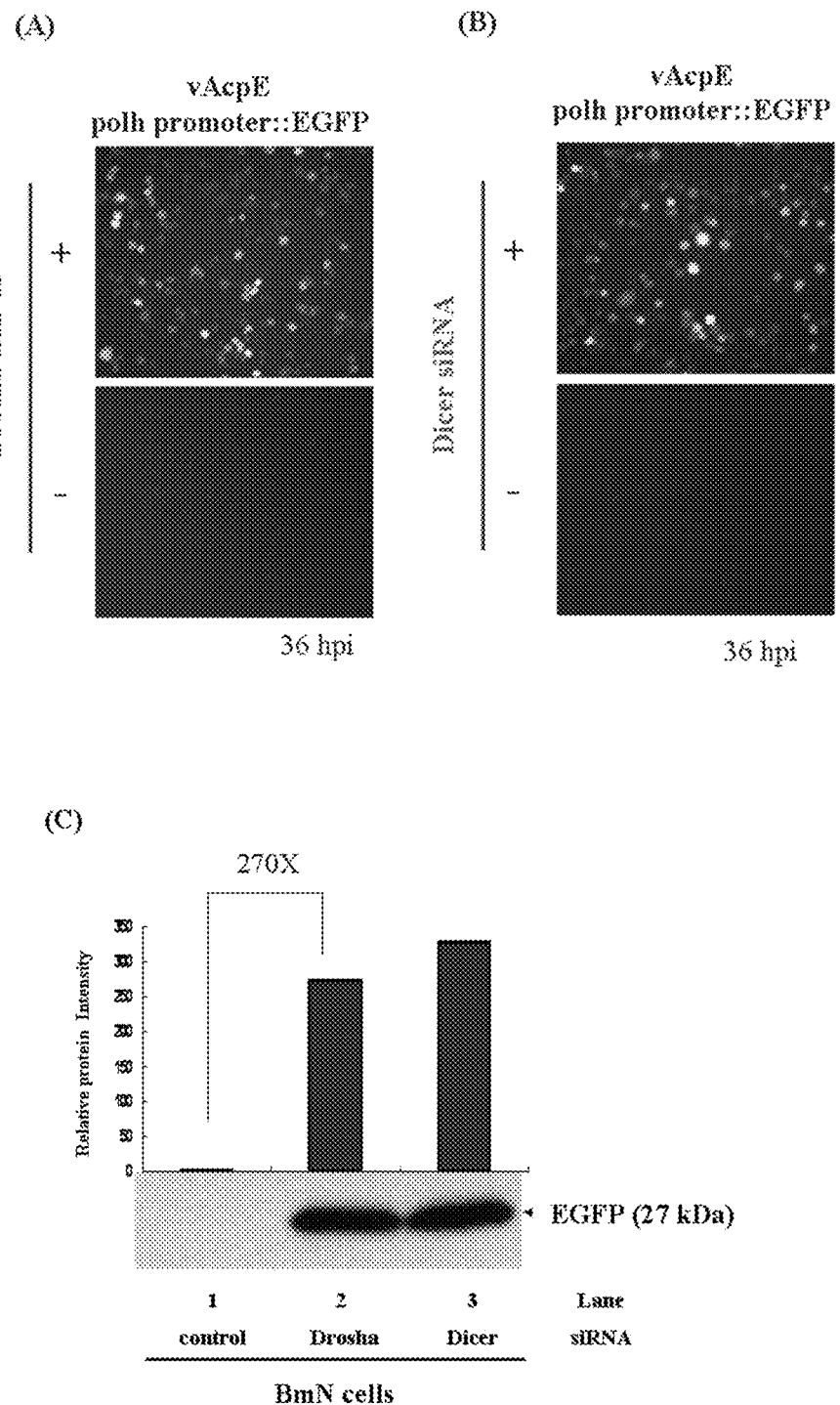
FIG. 6 is a set of fluorescent images, graph and blot showing that knockdown of endogenous drosha or dicer expression in BmN cells potentiated AcMNPV infection to very late stages. Cells were first transfected with the indicated siRNAs, and then infected with an AcMNPV carrying the GFP gene under the control of a very late polyhedrin promoter (vAcpE). Panel A: Fluorescence microscopic image of BmN cells treated with drosha siRNA. Panel B: Fluorescence microscopic image of BmN cells treated with dicer siRNA. Panel C: Western blot and a graph showing GFP expression in the BmN cells.
Figure 7:
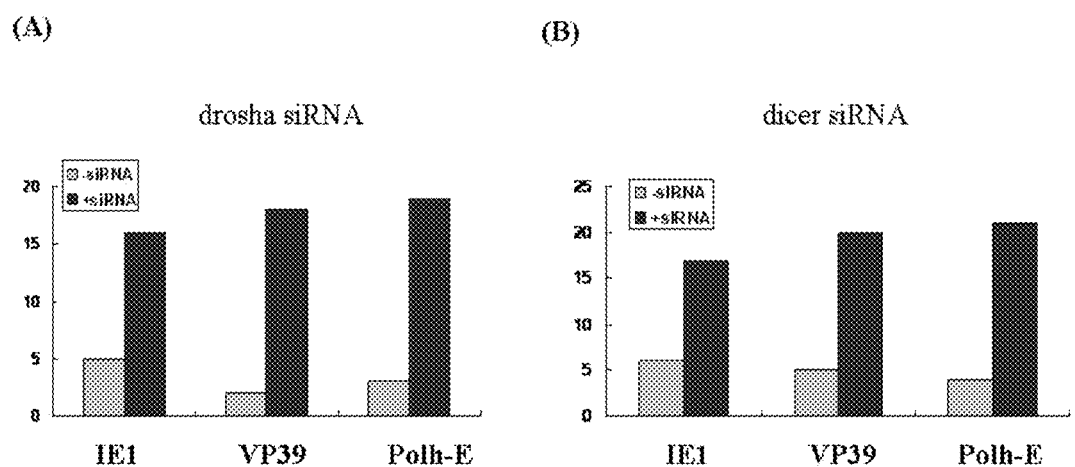
FIG. 7 is a set of bar graphs showing that the activities of three classes of AcMNPV promoters were increased in BmN cells transfected with drosha siRNA (Panel A) or dicer siRNA (Panel B).

It was unexpectedly discovered that inhibiting the expression of genes involved in miRNA pathway or host antiviral defense pathway in cells can enhance expression of baculovirus-transduced genes, efficiency of transduction and production of viral progenies.

Accordingly, described herein is a method for expressing a baculovirus-transduced gene in a cell by first introducing into a cell an agent that inhibits the endogenous miRNA pathway and/or the antiviral defense pathway of the cell, and then infecting the cell with a baculovirus carrying a gene to be expressed in the cell.

As used herein, the miRNA pathway refers to the pathway by which miRNAs are produced, processed and activated to regulate gene expression. The pathway includes, but are not limited to, expression of primary miRNAs, processing of the primary miRNAs to form precursor miRNAs, export of the precursor miRNAs from the nucleus to the cytoplasm, processing of the precursor miRNAs to form mature miRNAs, and incorporation of the mature miRNAs into RNA-induced silencing complexes. Agents that inhibit the miRNA pathway include agents that target and inhibit the function of any step or component in the miRNA pathway. For example, the miRNA pathway can be inhibited by an agent that blocks the expression or function of a protein in the pathway, e.g., Drosha, Dicer and Exportin-5.

The antiviral defense pathway refers to the mechanism or the series of responses by which a cell fights against viral infection. For example, the pathway can include the innate immunity system. Agents that inhibit antiviral defense pathway can include agents that target and inhibit the function of any step or component in the antiviral defense pathway. Such agent can be one that blocks the expression or function of a protein in the pathway, e.g., Toll-like receptor-2, STAT1, STATE, interleukin 7R, or Interleukin 1A.

Agents that can be used in the above-described methods include nucleic acid molecules that inhibit the expression or activity of a target gene related to the miRNA pathway or the antiviral defense pathway. These nucleic acid molecules include antisense nucleic acids, small inhibitory RNAs (siRNAs), ribozymes, and other modified nucleic acid molecules such as PNAs.

The nucleic acid molecules or constructs include dsRNA molecules including 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is identical or substantially identical to the first strand. The dsRNA molecules can be chemically synthesized, or can transcribed be in vitro from a DNA template, or in vivo from, e.g., shRNA. The dsRNA molecules can be designed using any method known in the art.

The nucleic acid molecules used in the methods described herein can include both siRNA and modified siRNA derivatives, e.g., siRNAs modified to alter a property such as the pharmacokinetics of the composition, for example, to increase half-life in the body, e.g., crosslinked siRNAs. siRNA derivatives can include siRNAs having two complementary strands of nucleic acid, such that the two strands are crosslinked. In some embodiments, the siRNA derivative can be conjugated to a biotin molecule (e.g., a photocleavable biotin), a peptide (e.g., a Tat peptide), a nanoparticle, a peptidomimetic, organic compounds (e.g., a dye such as a fluorescent dye), or dendrimer. The conjugation can be accomplished by methods known in the art, e.g., using the methods of Lambert et al., Drug Deliv. Rev.:47(1), 99-112 (2001); Fattal et al., J. Control Release 53(1-3):137-43 (1998); Schwab et al., Ann Oncol. 5 Suppl. 4:55-8 (1994); and Godard et al., Eur. J. Biochem. 232(2):404-10 (1995).

Synthetic siRNAs can be delivered into cells by methods known in the art, e.g., by cationic liposome transfection and electroporation. siRNAs can also be expressed within cells from recombinant DNA constructs.

An "antisense" nucleic acid can include a nucleotide sequence that is complementary to a "sense" nucleic acid encoding a protein, e.g., complementary to the coding strand of a double-stranded cDNA molecule. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence encoding the target gene (e.g., the 5' and 3' untranslated regions).

Antisense nucleic acids can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest). Based upon the sequences of target genes, one of skill in the art can easily choose and synthesize any of a number of appropriate antisense molecules for use in accordance with the present invention.

Target gene expression can be also be inhibited by targeting nucleotide sequences complementary to the regulatory region of the target gene (e.g., promoters and/or enhancers) to form triple helical structures that prevent transcription of the gene in target cells. See generally, Helene, C. Anticancer Drug Des. 6:569-84 (1991); Helene, C. Ann N.Y. Acad. Sci. 660:

27-36 (1992); and Maher, Bioassays 14:807-15 (1992). The potential sequences that can be targeted for triple helix formation can be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Ribozymes can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to the nucleotide sequence of a target cDNA, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel, D. and Szostak, J. W. Science 261:1411-1418 (1993).

The methods provided herein can be applied to any cell that can be infected or entered into by baculovirus, e.g., insect cells and mammalian cells.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are herein incorporated by reference in their entirety.

Example

Small interfering RNAs (siRNAs) were used to target different genes in insect and mammalian cells to assess their effects on the expression of genes transduced into the cells by baculovirus. Data demonstrated that knocking-down of particular genes can increase baculovirus-mediated transgene expression. These genes include drosha and dicer in insect and mammalian cells, and tlr2, stat1/6, and il-1a/7r in mammalian cells.

It was found that the expression of genes delivered via baculovirus transduction into mammalian cells increased upon silencing of either drosha or dicer expression. These results suggest that the endogenous RNAi pathway hinders the potential for baculovirus serving as an efficient gene delivery vehicle into mammalian cells.

Figure 8:
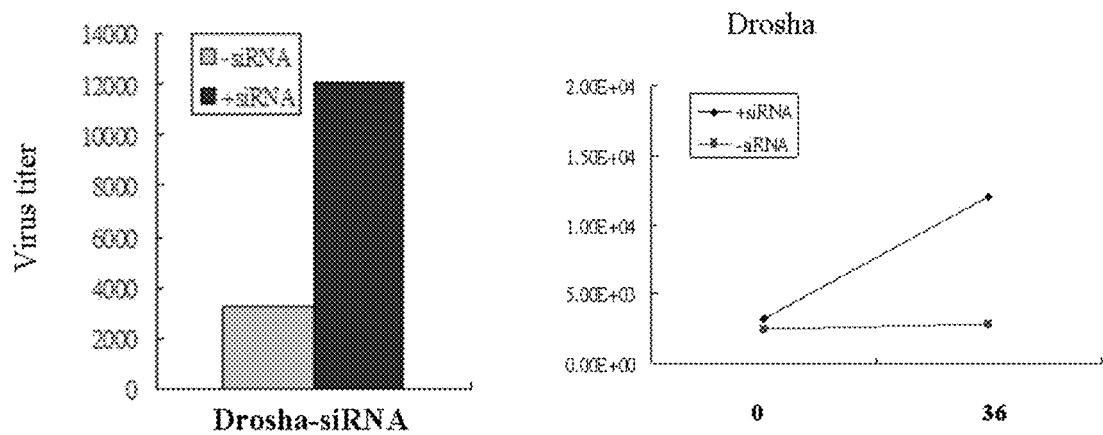
FIG. 8 is a set of graphs showing that more AcMNPV progenies were generated in BmN cells when the cells were first treated with drosha siRNA (Panel A) or dicer siRNA (Panel B).
Figure 8:
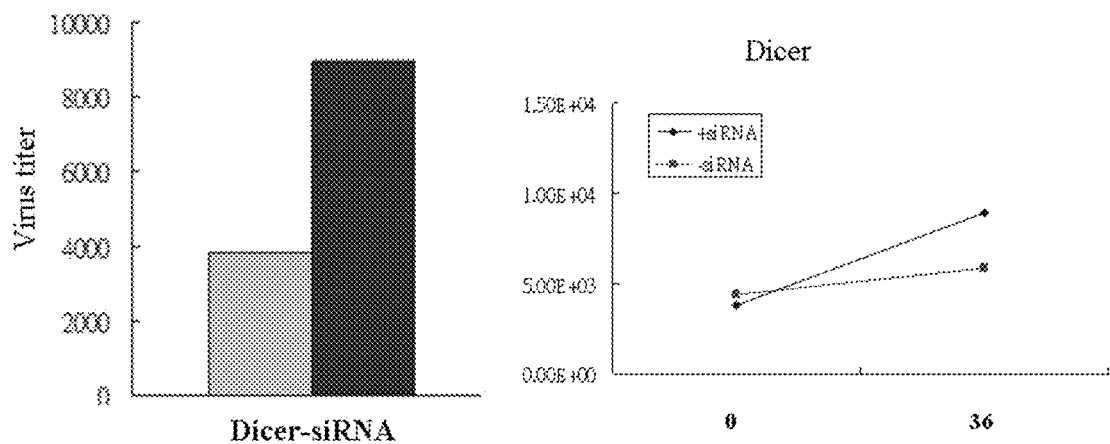

The expression of endogenous drosha and dicer was successfully silenced by siRNAs separately targeted to these two genes in insect silkworm BmN cells, mammalian osteosarcoma epithelial U-2OS and African green monkey epithelial VeroE6 cells. See FIG. 1, panels (A)-(C). The sequences of the siRNAs used are shown in Table 1 below. No significant cytotoxicity was detected in cells transfected with these siRNAs. See FIG. 2.

TABLE 1

Sequences of siRNAs

| siRNA target | Sequence |
|---|---|
| *Mammalian drosha* | AACGAGUAGGCUUCGUGACUU (SEQ ID NO: 1) |
| *Mammalian* dicer | UUUGUUGCGAGGCUGAUUC (SEQ ID NO: 2) |
| *Mammalian* control | UCAAGAAGCCAAGGAUAAU (SEQ ID NO: 3) |
| *B. mori drosha* | GGCATACGTAATGGGAAAG (SEQ ID NO: 4) |
| *B. mori* dicer | AGAGTAACTGTGGCTGATT (SEQ ID NO: 5) |
| *B. mori* control | UUCUCCGAACGUGUCACGUTT (SEQ ID NO: 6) |

U-2OS and VeroE6 cells with silenced drosha or dicer were transduced with recombinant baculovirus containing a green fluorescence gene under the control of a human cytomegalovirus immediate early promoter, i.e., the CMVie promoter. Fluorescent microscopic imaging showed that green fluorescence protein expression was increased in U-2OS cells in which drosha or dicer expression was silenced as compared to cells transfected with control siRNA in which drosha and dicer were expressed normally. See FIG. 3, panel A. Western blot analysis further confirmed this observation in both U-2OS and VeroE6 cells. See FIG. 3, panel B.

To obtain quantitative data, U-2OS and VeroE6 cells were first transfected with respective siRNAs and the transfected cells were subsequently transduced with recombinant baculovirus carrying a luciferase gene also under the control of the CMVie promoter. Results from the luciferase activity assay were consistent with the above-described western blot analysis. Namely, the expression of trans-gene delivered into cells by baculovirus was increased when endogenous drosha or dicer expression was knocked down. See FIG. 4.

In a parallel experiment, a reporter cassette was delivered into target cells by liposome instead of baculovirus transduction. In contrast to baculovirus transduction, the expression of the trans-gene delivered into VeroE6 cells by liposome increased in drosha-knockdown cells and decreased in dicer-knockdown cells. See FIG. 5. In U-2OS cells, the knockdown of drosha or dicer expression did not have any effect on the expression of the trans-gene delivered via liposome. Also see FIG. 5. These results suggest that the increase in trans-gene expression is unique in baculovirus-transduced cells, and that the endogenous RNAi pathway plays a role in the efficiency of baculovirus transduction into mammalian cells.

AcMNPV normally fails to establish a successful infection in silkworm BmN cells. When the expression of endogenous drosha or dicer was silenced in silkworm BmN cells, AcMNPV was able to proceed to the very late stage of a successful virus infection as evidenced by the activity of a very late polyhedrin promoter (i.e., vAcpE). See FIG. 6, panels A and B. Western blot analysis further confirmed this observation. See FIG. 6, panel C. In fact, all three classes of promoters of AcMNPV were stimulated when the expression of BmN drosha or dicer was knocked down. See FIG. 7, panels A and B. Further analysis demonstrated that more infectious virus particles were generated in drosha- or dicer-silenced BmN cells, suggesting that BmN cells became more susceptible to AcMNPV infection when endogenous drosha or dicer expression was silenced. See FIG. 8, panels A and B.

Figure 9:
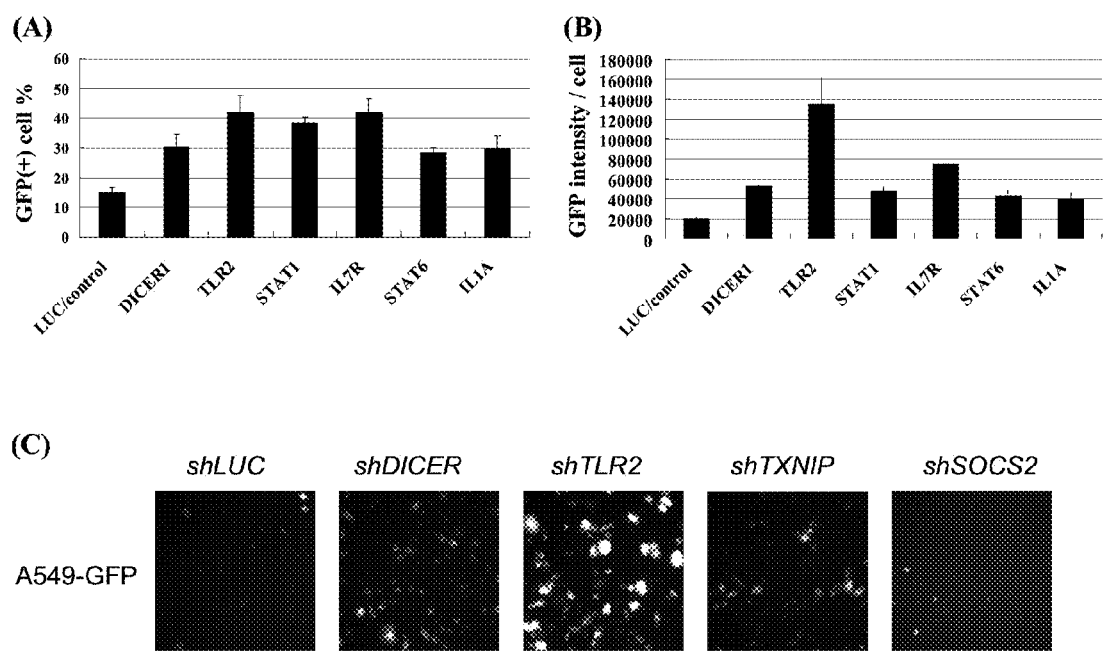
FIG. 9 is a set of graphs and fluorescent images showing that knockdown of genes associated with host antiviral defense enhanced baculovirus transduction efficiency and reporter gene (GFP) expression in A549 cells. A549 cells were first transduced via Lentivirus with shRNAs targeting the luciferase gene (negative control), dicer (positive control), toll-like receptor-2, STAT1, interleukin 7R, STAT6, or interleukin 1A. The cells were then transduced with a baculovirus carrying the GFP gene. Panel A: Transduction efficiency was measured by percentage of GFP positive cells. Panel B: Reporter gene expression was measured by GFP intensity. Panel C: Fluorescent images of shRNA-treated A549 cells transduced by the baculovirus.
Figure 10:
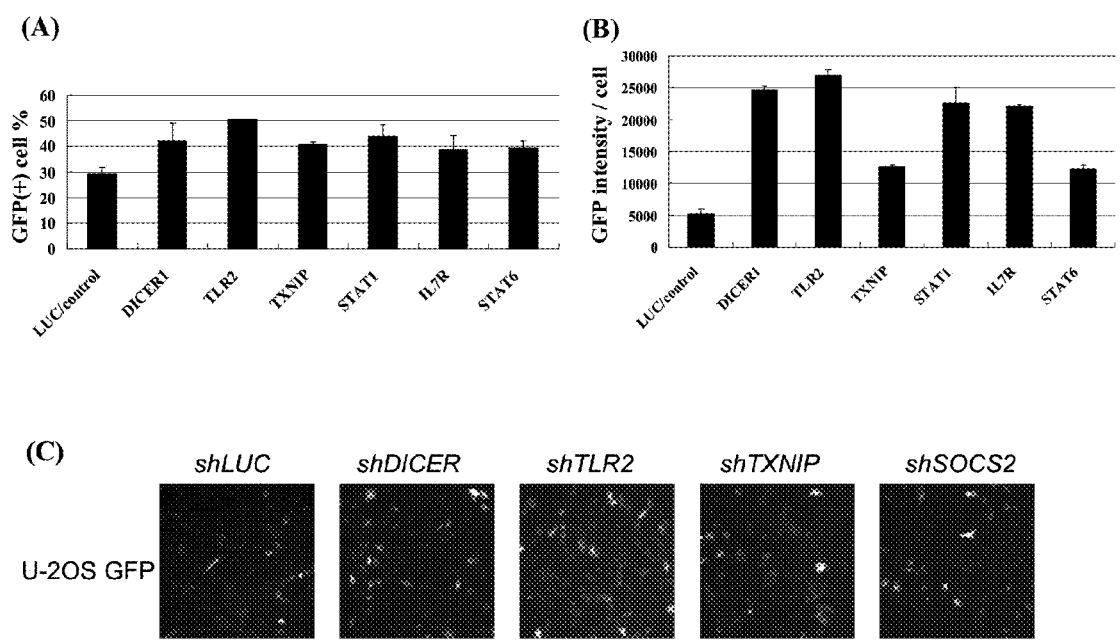
FIG. 10 is a set of graphs and fluorescent images showing that knockdown of genes related to host antiviral defense enhanced baculovirus reporter (GFP) expression in U-2OS cells, but did not significantly enhance transduction efficiency. U-2OS cells were first transduced via Lentivirus with shRNAs targeting luciferase (negative control), dicer (positive control), toll-like receptor-2, TXNIP, STAT1, interleukin 7R, and STAT6. The cells were then transduced with a baculovirus carrying the GFP gene. Panel A: Transduction efficiency was measured by percentage of GFP positive cells. Panel B: Reporter expression was measured by GFP intensity. Panel C: Fluorescent images of shRNA-treated U-2OS cells transduced by the baculovirus.

While baculovirus can efficiently transduce genes into many mammalian cell types, certain cell types, including Chinese hamster ovary cells (CHO) and human lung cancer cells (A549), show low or no trans-gene expression via baculovirus transduction. It was found that blocking host defense mechanism in these cells increased express of genes transduced by baculovirus. To block host defense mechanisms, specific shRNAs were expressed in A549 and CHO cell lines by lentivirus transduction. These shRNAs were designed to knock down the function of different host genes involved in host defense mechanisms. See Table 2. In A549 cells, baculovirus transduction efficiency and reporter gene expression were increased when some host innate immunity genes, TLR2, STAT1/6, and IL-1A/7R, were knocked down. See FIG. 9. Similar results were also found in U-2OS cell lines by using shRNAs against these genes. See FIG. 10.

TABLE 2

Sequences of shRNAs.

| shRNA target | Sequence |
| --- | --- |
| dicer | GCUGGCUGUAAAGUACGACUA (SEQ ID NO: 7) |
| txnip | GUGGUCUUUAACGACCCUGAA (SEQ ID NO: 8) |
| socs2 | CCAACUAAUCUUCGAAUCGAA (SEQ ID NO: 9) |
| tlr2 | GCACACGAAUACACAGUGUAA (SEQ ID NO: 10) |
| IL7R | CUGAUUGGAAAGAGCAAUAUA (SEQ ID NO: 11) |
| IL1A | CCACCCUCUAUCACUGACUUU (SEQ ID NO: 12) |
| stat1 | CUGGAAGAUUUACAAGAUGAA (SEQ ID NO: 13) |
| stat6 | GCCUUCUUAUGACCUUGGAAU (SEQ ID NO: 14) |
| control luc | CAAAUCACAGAAUCGUCGTU (SEQ ID NO: 15) |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for expressing a gene in a cell, the method comprising, introducing into a cell (i) an agent that inhibits one or both of miRNA pathway and antiviral defense pathway; and (ii) a baculovirus that contains a nucleic acid molecule including a gene operably linked to a promoter; and expressing the gene in the cell the agent inhibits expression of Drosha, Dicer, Toll-like receptor-2, STAT1, STAT6, interleukin 7R, or Interleukin 1A, the promoter being a CMV promoter.

2. The method of claim 1, wherein expression of the gene in the cell is increased as compared to that in the absence of the agent that inhibits miRNA pathway.

3. The method of claim 2, wherein the agent is a small inhibitory RNA (siRNA).

4. The method of claim 2, wherein the agent inhibits expression of Drosha or Dicer.

5. The method of claim 4, wherein the agent is an siRNA.

6. The method claim 1, wherein the cell is a vertebrate cell.

7. The method of claim 1, wherein the cell is an invertebrate cell.

8. The method of claim 5, wherein the cell is a mammalian cell.

9. The method of claim 8, wherein the promoter is a the CMVie promoter.

10. The method of claim 1, wherein the baculovirus is a *Autographa califormica* multicapsid nuclear polyhedrosis virus (AcMNPV).

11. The method of claim 1, wherein the agent is introduced into the cell before the baculovirus.

12. The method of claim 2, wherein the agent inhibits expression of Toll-like receptor-2, STAT1, STAT6, interleukin 7R, or Interleukin 1A.

13. The method of claim 12, wherein the agent is an siRNA.

14. The method of claim 13, wherein the cell is a mammalian cell and the promoter is the CMVie promoter.

\* \* \* \* \*

SEQUENCE LISTING

```
<160> NUMBER OF SEQ ID NOS: 15

<210> SEQ ID NO 1
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 1
aacgaguagg cuucgugacu u                                              21

<210> SEQ ID NO 2
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 2
uuuguugcga ggcugauuc                                                 19

<210> SEQ ID NO 3
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 3
ucaagaagcc aaggauaau                                                 19
```

```
<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
ggcatacgta atgggaaag                                              19

<210> SEQ ID NO 5
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 5
agagtaactg tggctgatt                                              19

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
uucuccgaac gugucacgut t                                           21

<210> SEQ ID NO 7
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 7
gcuggcugua aaguacgacu a                                           21

<210> SEQ ID NO 8
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 8
guggucuuua acgacccuga a                                           21

<210> SEQ ID NO 9
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 9
ccaacuaauc uucgaaucga a                                           21

<210> SEQ ID NO 10
<211> LENGTH: 21
<212> TYPE: RNA
<213> ORGANISM: Artificial sequence
<220> FEATURE:
<223> OTHER INFORMATION: Synthetic oligonucleotide
```

```
<400> SEQUENCE: 10
gcacacgaau acacagugua a                                                      21

<210> SEQ ID NO 11
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 11
cugauuggaa agagcaauau a                                                      21

<210> SEQ ID NO 12
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 12
ccacccucua ucacugacuu u                                                      21

<210> SEQ ID NO 13
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 13
cuggaagauu uacaagauga a                                                      21

<210> SEQ ID NO 14
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 14
gccuucuuau gaccuuggaa u                                                      21

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
caaaucacag aaucgucgtu                                                        20
```